(12) United States Patent
Amitai et al.

(10) Patent No.: US 8,412,313 B2
(45) Date of Patent: Apr. 2, 2013

(54) ECG DATA ACQUISITION DEVICE

(76) Inventors: David Amitai, Palo Alto, CA (US);
Assaf Amitai, Ramat GaN (IL)

( * ) Notice: Subject to any disclaimer, the term of this patent is extended or adjusted under 35 U.S.C. 154(b) by 0 days.

(21) Appl. No.: 13/293,888

(22) Filed: Nov. 10, 2011

(65) Prior Publication Data
US 2012/0059271 A1 Mar. 8, 2012

Related U.S. Application Data

(62) Division of application No. 12/191,923, filed on Aug. 14, 2008, now Pat. No. 8,082,025.

(51) Int. Cl.
*A61B 5/0404* (2006.01)
(52) U.S. Cl. .......................... 600/509; 600/523
(58) Field of Classification Search .................. 600/509
See application file for complete search history.

(56) References Cited

U.S. PATENT DOCUMENTS

| | | | | |
|---|---|---|---|---|
| 5,343,869 A | * | 9/1994 | Pross et al. | 600/301 |
| 2003/0208109 A1 | * | 11/2003 | David et al. | 600/300 |
| 2005/0101875 A1 | * | 5/2005 | Semler et al. | 600/509 |
| 2009/0270747 A1 | * | 10/2009 | van Dam et al. | 600/509 |

* cited by examiner

*Primary Examiner* — Niketa Patel
*Assistant Examiner* — Hiba El-Kaissi
(74) *Attorney, Agent, or Firm* — Calvin B. Ward (57) ABSTRACT

An apparatus for generating ECG recordings and a method for using the same are disclosed. The apparatus includes a handheld device and a controller. The handheld device has first, second, third, and fourth electrodes on an outer surface of the handheld device. The controller records signals from the first, second, third, and fourth electrodes and generates an ECG recording from the signals. The controller also provides placement information regarding locations on a user's body that are to be brought into contact with the first, second, third, and fourth electrodes while the controller records the signals. The handheld device can include a cellular telephone or a PDA. The controller stores an exemplary normal ECG recording, and compares a newly generated ECG recording with the stored ECG recording and generates an indication that indicates whether the newly generated ECG recording is consistent with the stored ECG recording.

15 Claims, 4 Drawing Sheets

ECG DATA ACQUISITION DEVICE

CROSS REFERENCE TO RELATED APPLICATIONS

This is a divisional of U.S. patent application Ser. No. 12/191,923 filed on Aug. 14, 2008 issued on Dec. 20, 2011 as U.S. Pat. No. 8,082,025.

BACKGROUND OF THE INVENTION

A number of systems that utilize remote ECG measurements to analyze a cardiac patient's condition have been proposed. These systems include some form of ECG electrodes that are attached to the patient's body and connected to a local processor carried by the patient. The local processor typically includes a transmitter that relays the measurements from the unit worn by the patient to a physician at a remote location. The relay mechanism can utilize a telephone line, either land or cellular, or some form of dedicated transmitter.

This system requires that electrodes be attached to the patient's body. To provide a full 12 lead ECG recording set, electrodes are typically attached to the patient's upper and lower limbs, as well as to a number of locations on the torso. If the patient is in a setting in which the patient has only limited mobility, such a set of attached electrodes may be acceptable; however, if the patient is fully mobile and attending to his or her normal routine outside of a medical environment, temporary or permanent attachment of the electrodes is not usually acceptable and involves a fair amount of discomfort. Furthermore, the electrodes must be removed when the patient bathes. Hence, some arrangement in which the patient or a caregiver places the electrodes on the patient's body at the time an ECG is to be recorded is needed.

A system based on the use of adhesively coated electrodes such as those utilized in normal ECG measurements presents problems from a logistical and cost point of view. The individual electrodes are only usable for a small number of measurements before the adhesive fails. Furthermore, the repeated placement and removal of the electrodes can cause patient discomfort, particularly in patients having body hair in the areas to which the electrodes must be attached.

Systems that utilize electrodes that are held against the body rather than being adhesively attached have been proposed. For example, U.S. Pat. No. 7,112,175 discloses a "glove" having electrodes on the fingertips. If the glove is correctly positioned, a number of ECG measurements can be made; however, the device assumes a constant relationship between the dimensions of the glove and the corresponding ECG measurement points on the patient's body, since the electrode positions are fixed relative to one another. In addition, not all of the measurements provided by the conventional lead ECG tests are provided by the glove.

Finally, the glove must be connected by cables to the transmitter that receives the data and either processes the data or transmits the data to a central processing system. While such arrangements are feasible in the confines of a patient's home, this type of system becomes problematic if the patient is at work or traveling. In this regard, it should be noted that a cardiac patient who is going about his or her normal life may detect an irregularity at any time and wish to verify that he or she is not suffering a cardiac event. The event can occur in any of a number of settings that do not lend themselves to providing a monitoring apparatus and leads for connecting the patient to the apparatus.

SUMMARY OF THE INVENTION

The present invention includes an apparatus for generating ECG recordings and a method for using the same. The apparatus includes a handheld device and a controller. The handheld device has first, second, third, and fourth electrodes on an outer surface of the handheld device. The controller records signals from the first, second, third, and fourth electrodes and generates an ECG recording from the signals. The controller also provides placement information regarding locations on a user's body that are to be brought into contact with the first, second, third, and fourth electrodes while the controller records the signals. The handheld device can include a cellular telephone or a PDA. In one aspect of the invention, the apparatus also includes an adapter that connects four ECG leads to the apparatus, the controller utilizing the four ECG leads in combination with the fifth electrode to measure a conventional ECG recording.

In another aspect of the invention, the controller stores an exemplary baseline ECG recording, and the controller compares a newly generated ECG recording with the stored ECG recording and generates an indication if the newly generated ECG recording is consistent with the stored ECG recording. The exemplary baseline ECG recording could be a previously recorded ECG recording or a signal derived from a plurality of previously recorded ECG recordings.

In another aspect of the invention, the apparatus includes a communication device that sends and receives messages from an external facility. The controllers communicate the newly recorded ECG recording to the external facility if the indication indicates that the newly generated ECG recording is inconsistent with the stored ECG recording.

In yet another aspect of the invention, the apparatus includes a microphone and speaker. The controller communicates instructions to the user via the speaker and receives communications from the user via the microphone while the controller generates the ECG recording. The apparatus could also include a buzzer and/or vibrator that causes the apparatus to vibrate when the vibrator is activated. The controller actuates the buzzer and/or vibrator when the controller is generating an ECG recording. The microphone can also be utilized to record heart sounds.

In another aspect of the invention, the apparatus includes a circuit for determining if the first, second, third, and fourth electrodes are in contact with the user's body.

The apparatus can be utilized to provide patient generated ECG recordings that replicate the standard lead recordings and are approximations to the conventional Precordial ECG recordings. In the method of the present invention, the patient is provided with an apparatus as described above. The patient grips the handheld device such that the first and second electrodes are in contact with a first hand of the patient such that the first and second electrodes contact different locations on the first hand. Simultaneously the patient makes contact with the third electrode on the patient's other hand. During the measurement, the patient places the fourth electrode at a predetermined point on the patient's body, the predetermined point depending on the particular ECG recording being generated. The signals as a function of time between the first electrode and each of the second, third, and fourth electrodes are measured and converted into the ECG recording.

DETAILED DESCRIPTION OF THE PREFERRED EMBODIMENTS OF THE INVENTION

Figure 1:
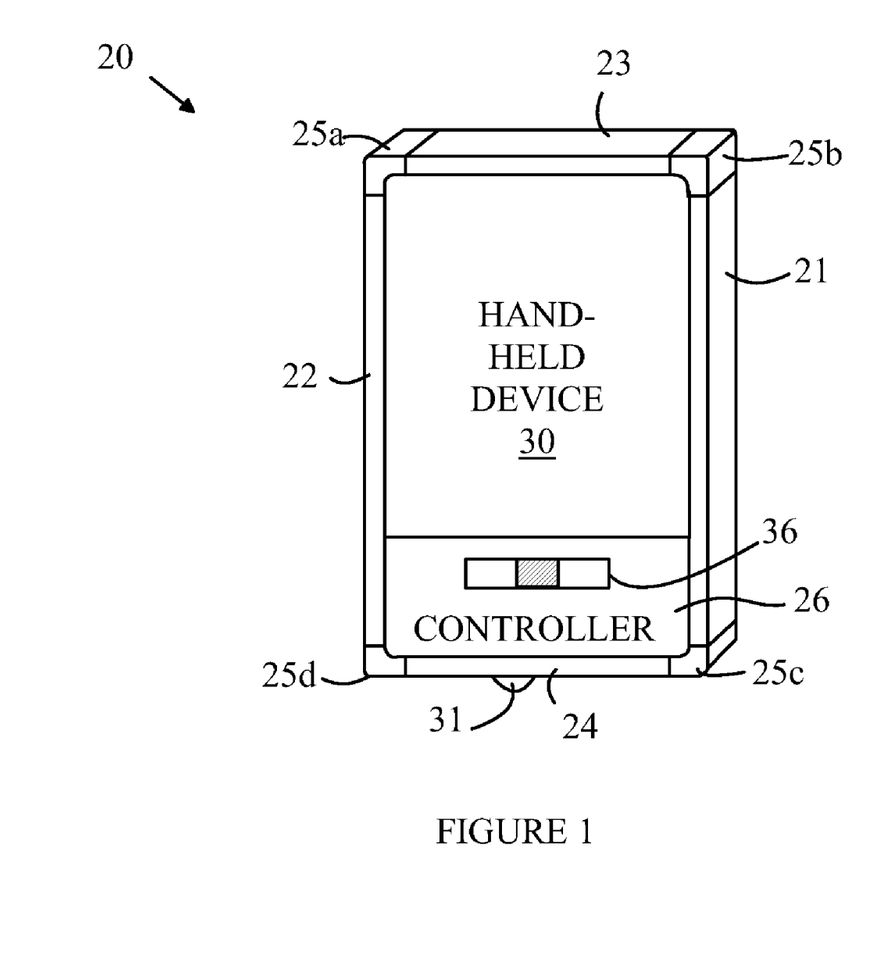
FIG. 1 illustrates one embodiment of an ECG data acquisition device according to the present invention.

The present invention is based on the observation that a full ECG can be measured with a four terminal device if the measurements are made one at a time. Refer now to FIG. 1, which illustrates one embodiment of an ECG data acquisition device according to the present invention. ECG data acquisition device 20 may be viewed as comprising two components. The first component is a handheld device 30 such as a cellular telephone or personal data assistant (PDA). The second component, referred to as the electrode component, is a set of electrodes and a controller that are attached to the outside of handheld device 30. The electrodes are shown at 21-24, respectively, and are separated from one another electrically by insulating the insulating regions shown at 25a-25d. In one aspect of the invention, one or more of the insulating regions include an elastic member that allows the electrode component to be reversibly attached to the handheld device 30.

The functions provided by controller 26 and switch 36 will be discussed in more detail below. For the purposes of the present discussion, it is sufficient to note that the electrodes are connected to a controller 26 and that controller 26 communicates with the data processor in handheld device 30. In addition, controller 26 provides the electrical interface for the signals communicated by electrodes 21-24 and preprocesses those signals. Controller 26 is connected to handheld device 30 through one of the conventional signal connections that are typically included in handheld devices. The connections may include direct electrical connections via an existing port such as an USB port or wireless connections such as Bluetooth.

The manner in which ECG data acquisition device 20 is used to generate a 12 lead ECG will now be explained in more detail. A conventional 12 lead ECG involves the placement of ten electrodes at designated places on the patient's body. The signals from these ten electrodes are then processed to generate 12 graphs of voltage as a function of time that are called the ECG chart or diagram. In the conventional ECG measurements, four electrodes are attached to the patient's limbs, typically on the wrists and ankles. These electrodes are referred to as the standard lead electrodes. The remaining six electrodes are attached to specific points on the patient's chest. These electrodes are referred to as the Precordial electrodes.

A 12 trace ECG diagram is obtained using ECG data acquisition device 20 by holding the ECG data acquisition device with both hands and pressing electrode 24 against the appropriate place on the patient's body. In one embodiment, electrodes 21 and 22 are held in the right hand with the thumb on electrode 21 and the right index finger on electrode 22. The left index finger or any part of the left palm is held on electrode 23. It should be noted that electrode 22 can be touched with other fingers of the right hand besides the index finger. Electrode 21 can also be touched with other fingers or part of the right hand. The type of measurement being performed can be communicated to controller 26 through mode switch 36, which has a plurality of predetermined positions. For the standard lead measurements, mode switch 36 is set to a first position, and electrode 24 is placed against any point of the left leg or the lower abdomen. For the Precordial measurements, mode switch 36 is set to a second position, and electrode 24 is placed sequentially at each of the Precordial positions on the patient's chest.

As noted above, the four conventional electrodes are placed on the left and right wrists and the left and right ankles. In the present invention, these measurements are provided by using the potential from the right index finger, i.e., electrode 22, in place of the potential from the right wrist, the potential from the right thumb, i.e., electrode 21 in place of the potential from the right ankle, the potential from the left index finger, i.e., electrode 23 in place of the potential from the left wrist, and the potential from the left leg, i.e., electrode 24 in place of the potential from the left ankle.

Denote the potential from electrode 21 by $\Phi_g$, the potential from electrode 22 by $\Phi_r$, the potential from electrode 23 by $\Phi_l$, and the potential from electrode 24 by $\Phi_f$. The first three standard lead traces are given by $$I = \Phi_l - \Phi_r$$

$$II = \Phi_f - \Phi_r$$

$$III = \Phi_f - \Phi_l = II - I$$

Three additional traces are generated by utilizing weighted sums and differences of the potentials, namely $$aVR = \Phi r - (\Phi_l + \Phi_f)/2 = -(I+II)/2$$

$$aVL = \Phi_l - (\Phi_r + \Phi_f)/2 = I - II/2$$

$$aVF = \Phi_f - (\Phi_l + \Phi_f)/2 = I - I/2$$

In one embodiment of the present invention, controller 26 performs the various potential measurements and calculations to provide the six traces in question. However, embodiments in which the computations are carried out by the processor in the handheld device or at an external facility connected to the handheld device can also be constructed.

The remaining six traces are the Precordial traces (V1 . . . V6). In the conventional Precordial measurements, each trace is generated by forming the average of the potentials from the right and left wrists and the left leg (this averaged potential is known as the Central-Terminal $\Phi_{CT}$) and then measuring the difference between $\Phi_{CT}$ and a potential, $\Phi_i$, detected by an electrode at a corresponding point on the patient's chest. A different predetermined point on the chest being used for each of the six traces. Again, the right leg is used as the ground reference for each of these potentials. Namely $Vi = \Phi_i - (\Phi r + \Phi_l + \Phi_f)/3$.

In the present invention, a novel approximation to the conventional Precordial traces is obtained by using the average of the potentials recorded from the left and right index fingers in place of $\Phi_{CT}$. The averaging function can be performed in hardware that is introduced into the signal paths when the mode switch is set to the Precordial position or by software in the controller or handheld device. This potential will be denoted by $\Phi_{AT}$ in the following discussion. The approximations utilized in the present invention for the Precordial traces are given by $$R_i = \Phi_i - \Phi_{AT} = \Phi_i - (\Phi r + \Phi_l)/2.$$

It can be shown that $R_i$ is a good approximation of $V_i$.

The potential from the right thumb is again utilized as the ground reference. For each measurement, the device is placed against the appropriate location on the chest such that electrode 24 is in contact with the location in question. It should be noted that for these tests, electrode 24 may include a protrusion 31 surrounded by an insulating area that limits the area of contact so that only the desired location is in contact with electrode 24.

As noted above, the $R_i$ are approximations to the conventional $V_i$ traces. In some cases, corrections to the Precordial signal measured $R_i$ to compensate for the missing leg potential $\Phi_f$ may be desirable. If there are no significant changes between different Cardiac cycles of the aVF trace, the data recorded from the previous standard lead measurement of aVF can be utilized to correct the $R_i$ measurements to obtain a better approximation of the $V_i$ traces according to the relationship:

$$V_i = R_i - aVF/3 = \Phi_r - (\Phi r + \Phi_f + \Phi_f)/3$$

This method deviates from the conventional measurement in that the signals are not recorded simultaneously. When the ECG signals change significantly in time, the approximation to $V_i$ may actually be less accurate than the $R_i$. Such changes occur during an arrhythmia. This mode of operation for the Precordial leads measurements requires that standard leads be measured a short predetermined time before or after the Precordial measurements to ensure that a valid aVF signal is obtained when performing the aVF correction. If the person for some reason did not measure the standard leads, the device detects it and notifies via an alarm so that the person can perform the standard leads measurements.

Figure 2:
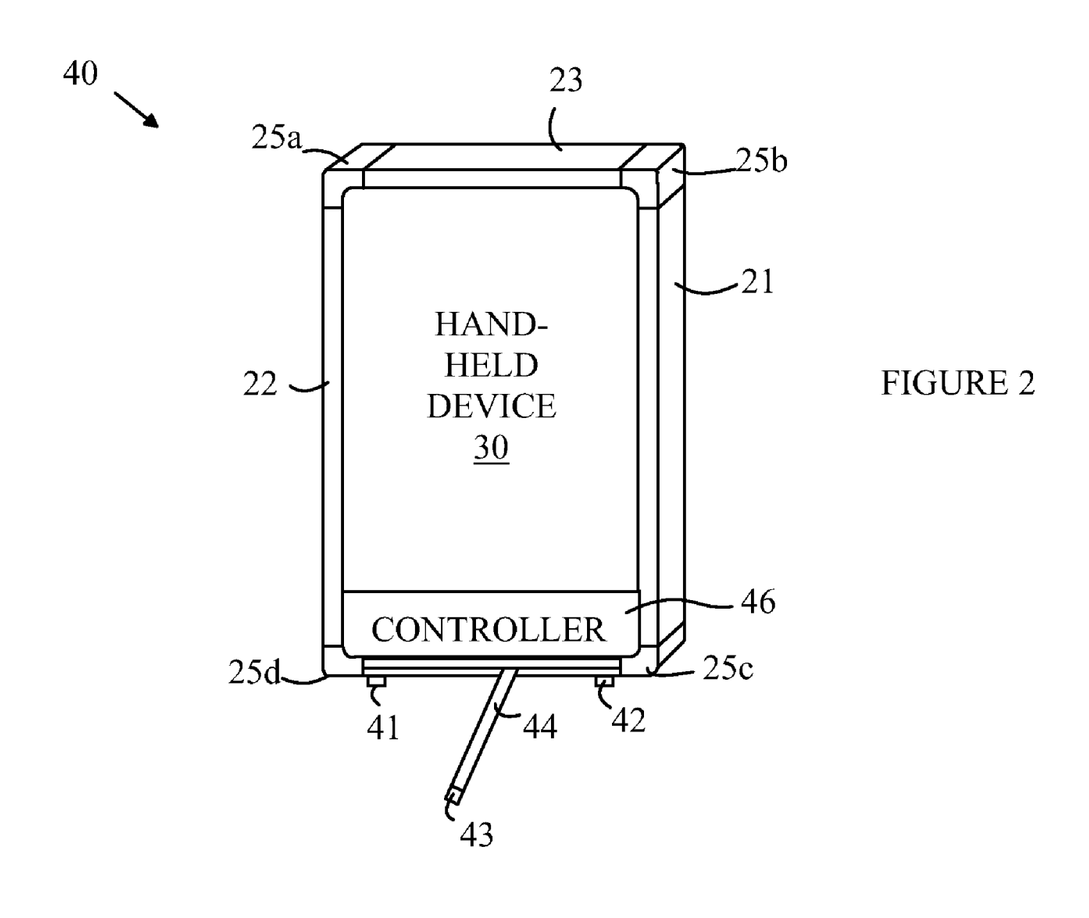
FIG. 2 illustrates another embodiment of an ECG data acquisition device according to the present invention.

In one embodiment of the present invention, the Precordial traces are measured one at a time. However, embodiments in which a plurality of measurements is made simultaneously can also be constructed. Refer now to FIG. 2, which illustrates another embodiment of an ECG data acquisition device according to the present invention. ECG data acquisition device 40 is similar to ECG data acquisition device 20 discussed above with reference to FIG. 1 in that it includes a handheld device that receives data from a plurality of electrodes via a controller 46 which can include a mode switch such as switch 36 discussed above or utilize other input devices for indicating the mode of operation. In ECG data acquisition device 40, electrode 24 of ECG data acquisition device 20 has been replaced by a Precordial electrode structure having a plurality of electrodes that are spaced such that each electrode makes contact with a different Precordial location when ECG data acquisition device 40 is properly placed on the patient's chest. In the embodiment shown in FIG. 2, the Precordial electrode structure includes two fixed electrodes shown at 41 and 42 and a moveable member 44 that pivots within the Precordial electrode structure to provide additional electrodes such as electrode 43 when member 44 is deployed from its storage position within the Precordial electrode structure. When the standard lead traces are being generated moveable member 44 is stored within the Precordial electrode structure and electrodes 41 and 42 are pressed against the patient's leg. During the standard lead measurements, electrodes 41 and 42 are connected together to form a single electrode.

As noted above, the traces obtained by using the present invention are approximations to those obtained with a conventional ECG system in the case of the Precordial measurements. For many purposes, the differences between the conventional and approximation traces are insignificant in that the purpose of the test is to detect a change in the patient's condition. For example, the portable ECG apparatus of the present invention can be used by the patient to determine that symptoms experienced by the patient are the result of a cardiac problem as opposed to some other problem. In this situation, a comparison of the ECG traces during the symptomatic period with those previously measured with the same device when the patient was not symptomatic can be sufficient to determine if a potential cardiac problem has arisen. In such an application, the handheld device stores the previously measured traces (or has access to these traces by a network connection) and compares those traces to the newly measured traces during the symptomatic period to determine if a significant change has occurred in the traces. If the new traces differ from the stored traces by more than a predetermined manner, the patient's results can be transferred via the handheld device to the medical facility responsible for the patient's care and the patient notified that a problem exists. If the traces are not significantly different from the stored trace, the patient can be notified of that result by the handheld device and the patient can then continue with his or her normal activities. In addition, in many cases a comparison to previously taken traces is not needed, and a diagnosis can be done solely based on the current traces.

To carry out such a comparison, the handheld device needs to store one or more sets of traces taken with the present invention and information concerning the expected variability of the traces from measurement to measurement during non-symptomatic periods. Traces taken during the non-symptomatic periods will be referred to as baseline approximation traces in the following discussion. A number of such baseline approximation trace sets can be generated by the patient in the doctor's office during a training period in which the patient is taught to use the present invention by a nurse. The handheld device can then generate an average baseline approximation trace set and a measure of the statistical variability of the traces in the set. This average normal approximation trace set can then be used in the field as the comparison trace set with which new approximation trace sets are compared to determine if the patient's heart has undergone a significant change.

In one aspect of the present invention, each time the patient acquires a new set of traces with the present invention, the new set is stored in the handheld device or the controller. Periodically, these stored traces are readout and transmitted to the medical facility that is responsible for the patient's care. These traces can then be analyzed in a more detailed manner to provide data on the functioning of the patient's heart over an extended period of time during normal activities. These traces can also be analyzed statistically to provide a new average normal approximation trace set for use in comparing new traces generated by the patient.

In another aspect of the present invention, each time the patient records a new set of traces with the handheld device, the patient also enters textual material on his handheld device describing the conditions that caused the patient to make the measurement, the patient's activity level, etc. This information is stored with the traces and readout when the recorded traces are readout. The textual information can be useful in analyzing the recorded measurements. For example, a comparison of all of the traces taken after the patient has exercised can be analyzed together to provide information on the manner in which the patient's heart is responding to such stresses.

Figure 3:
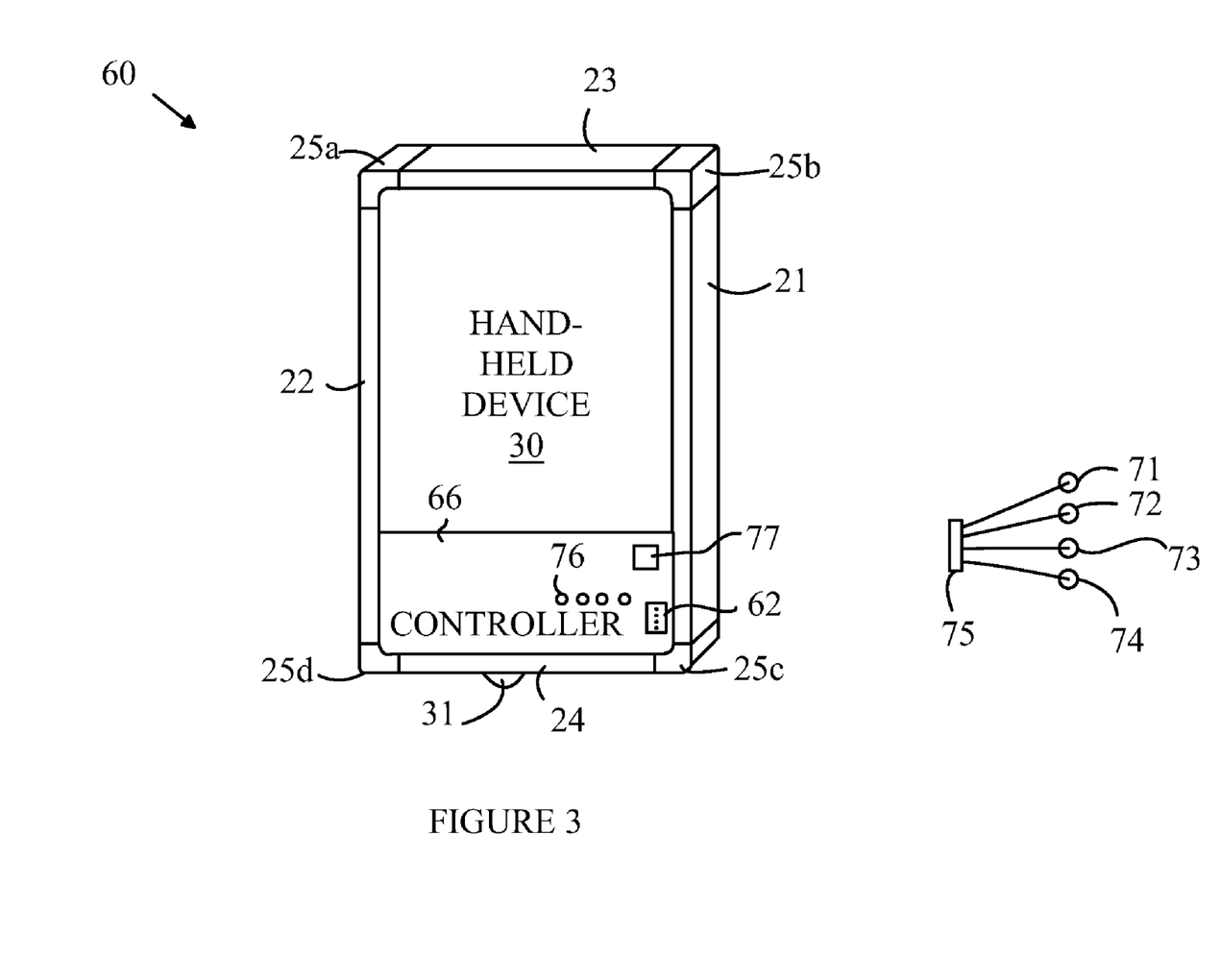
FIG. 3 illustrates another embodiment of an ECG data acquisition device according to the present invention.

In some cases, the differences between the approximation traces and the conventional traces may be important. In another aspect of the present invention, the controller also includes a socket for connecting four conventional test electrodes. Refer now to FIG. 3, which illustrates another embodiment of an ECG data acquisition device according to the present invention. ECG data acquisition device 60 is similar to ECG data acquisition device 20 discussed above, and hence, those elements of ECG data acquisition device 60 that perform functions that are analogous to functions performed by elements of ECG data acquisition device 20 have been given the same numerical definitions and will not be discussed in detail here. In ECG data acquisition device 60, controller 66 includes a port 62 that accepts a plug 75 that includes four conventional ECG leads 71-74. When plug 75 is inserted into port 62, controller 66 disconnects and replaces the signals from electrodes 21-23 with signals derived from leads 71-74 and generates the conventional Central-Terminal signal $\Phi_{CT}$ for use in performing the Precordial measurements.

During the recording of data utilizing the conventional electrodes, the conventional electrodes are attached to the patient in the same manner as the standard electrodes are connected during a conventional ECG measurement, i.e., on the patient's ankles and wrists. The standard lead measurements are made in the conventional manner using only these four electrodes. During the Precordial trace measurements, the device is placed in the Precordial mode by utilizing mode switch 36 or other input command to the controller. Electrode 24 is placed at each of the Precordial points on the patient's chest and a conventional ECG trace is generated utilizing the signals from four standard leads connected to port 62 and the signal from electrode 24.

Hence, when the four standard electrodes are connected to ECG data acquisition device 60 a set of conventional ECG traces can be generated by using the signals from these electrodes and electrode 24. These traces can be used for two purposes. First, if the approximation traces indicate that the patient's condition has changed significantly, the patient's doctor may wish to immediately measure a conventional set of ECG traces to provide a more detailed diagnosis of the patient's condition as close in time as possible to the event that caused the patient to record the approximation traces. In this situation, the patient, or a third party, can place the conventional leads on the patient's wrists and ankles so that the patient, or the third party, can record the conventional traces for transmission to the doctor using the handheld device, since any signals from electrodes 21-23 are ignored by the controller when plug 75 has been inserted into port 62, the third party can safely hold the device without having his or her own ECG signals interfering with the measurements.

Figure 4:
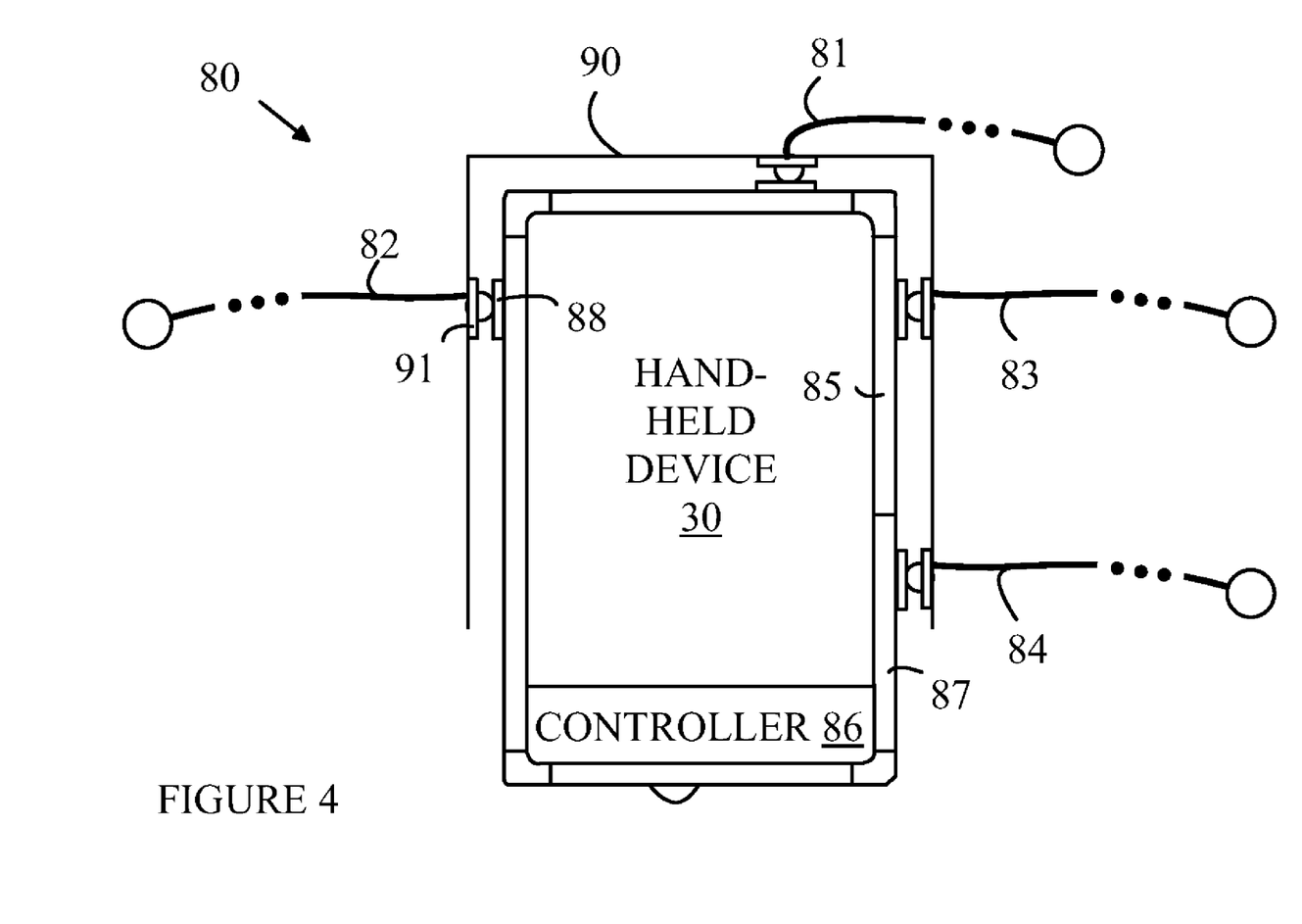
FIG. 4 illustrates another embodiment of an ECG data acquisition device according to the present invention.

The standard electrode leads must have several feet of wire to connect the electrodes to the ECG data acquisition device. These leads present a storage problem when not in use. In one embodiment of the present invention, the standard lead electrodes are stored in a rigid sleeve that also provides the connection to the ECG data acquisition device. Refer now to FIG. 4, which illustrates an embodiment of the present invention that utilizes a sleeve as the connector to the ECG data acquisition device. ECG data acquisition device 80 operates in a manner analogous to that described above with respect to ECG data acquisition device 60. When the standard lead electrodes are connected to ECG data acquisition device 80, controller 86 operates in a manner to provide the conventional ECG measurements as described above. The standard lead electrodes 81-84 are connected to a sleeve 90 that can also be used to store the electrodes when the electrodes are not connected to ECG data acquisition device 80. Sleeve 90 includes four contact members that make electrical contact with pads on the outer surface of ECG data acquisition device 80 when sleeve 90 is slipped over ECG data acquisition device 80. Each contact member includes a spring-loaded contact. An exemplary contact member 91 is shown in contact with a mating contact pad 88 in the drawing. In one aspect of the invention, the mating contact pads are disposed on the outer surface of the electrodes that are gripped by the user during the normal operation (i.e., the non-standard lead mode) of the invention. In this case, one of the outer electrodes is divided into two electrically isolated portions as shown at 85 and 87. One of the contacts can include a switch or other sensor that detects the connection of sleeve 90 and causes controller 86 to alter its functioning accordingly.

In one aspect of the invention, the handheld device stores the conventional traces recorded by ECG data acquisition device 60 during non-symptomatic periods with the newly recorded traces to determine if the difference in the conventional traces is also significant. These traces can be used to calibrate the approximation traces. By comparing the traces obtained with the conventional electrodes with the approximation traces, the differences can be determined, and in some cases, corrected. For example, a linear model that relates each standard trace to a linear combination of the approximation traces can be generated by determining the weighting coefficients applied to each of the approximation traces that provides the best fit to the data measured with both types of electrodes.

The controller of the present invention can utilize the data entry mechanism and display of the handheld device to reduce the circuitry needed to implement the controller. Many handheld devices include a keyboard or an emulated keyboard on a touch screen. In addition, many handheld devices include a port for connecting the handheld device to a computer so that the handheld device can synchronize certain files on the handheld device with corresponding files on the computer. The port can be a wireless connection such as Bluetooth or WiFi or a wired connection such as a USB port. By altering the code in the handheld device, the controller of the present invention can take over the processor in the handheld device during ECG measurements and transmissions. Hence, the handheld device can provide the interface to the medical facility either through the Internet or the local wireless telephone network.

The above-described embodiments of the present invention utilize an electrode system and controller that are attached to an existing handheld device such as a cellular telephone or handheld computer PDA. However, embodiments in which the present invention is built into a handheld device and the electrodes are part of the case of that device can also be constructed. For example, an existing PDA or cellular telephone could be reprogrammed to perform the signal acquisition and computation functions of the controllers discussed above. The case of the existing PDA or cellular phone would be replaced by a case having the electrodes described above. For the purposes of this discussion, a handheld device is defined to be any computing device that is held in the user's hand and that can be positioned on the user's body to make the measurements described above.

The above-described embodiments require that the controller be able to detect the presence of the user and determine that the user is holding the device in an acceptable manner to provide sufficient electrical connections between the user and the present invention. In addition, the device must be able to signal the user when a measurement begins and ends, so that the user knows when to proceed to the next measurement point. In one embodiment of the present invention, electrodes 21-24 include pressure sensors that detect the force that the user is applying to the device. For example, electrodes 21-24 can include strain gauges that measure the force applied to the electrodes. In another embodiment, the controller measures the capacitance or resistance between the various electrodes. When the user is holding the device with the required pressure, the capacitance of the user's body alters the capacitance measured between the ground electrode and each of the electrodes in question. Similarly, the user's body presents a finite resistance between each pair of electrodes that can be measured. In one aspect of the invention, the controller activates an alarm to notify the patient that the controller detected that the patient's hands or legs are touching each other or another part of the patient's body to prevent such contact from interfering with the measurements.

Finally, the controller can look for a missing signal on any of the electrodes and notify the user that the device is positioned incorrectly. If the controller does not detect a minimum number of cardiac cycles, the controller can notify the user to continue to hold the device or to repeat the recording.

During a series of measurements, the present invention communicates with the user at a number of points in the measurement process for each measurement. First, the present invention must communicate the positioning of the invention with respect to the user's body for the current measurement. Once the device is positioned properly, the user must communicate this fact to the present invention so that the present invention can initiate the desired measurement. At this point, the present invention verifies that the user is holding the present invention in the prescribed manner by using one of the measurements discussed above. If the measurements are consistent with the present invention being properly positioned, the present invention initiates the current measurement. If not, the present invention signals the user to correct the problem.

The present invention also preferably generates a signal that lets the user know that a trace is being recorded so that the user does not move the present invention before the trace is finished. When the measurement is finished, the present invention must signal the user that the measurement has been completed and provide the setup directions to the user for the next measurement.

In embodiments that include the speaker, display, and microphone components of a cellular telephone or PDA, these components can be utilized in the communication process. For example, the positioning of the present invention relative to the patient's body can be displayed graphically on the display. Similarly, the user can communicate with the present invention using the microphone to provide voice commands that are interpreted by the processor in the cellular phone or PDA. In this regard, it should be noted that voice activated call initiation is a common feature in modern cell phones. Similarly, the present invention can communicate with the user via the speaker. It should also be noted that many cellular telephones have a vibrate mode that can also be utilized for communication. For example, when a measurement is being made, the present invention can vibrate. When the vibration terminates, the user knows that the measurement is finished.

Refer again to FIG. 3. In one embodiment of the present invention, controller 66 includes a number of indicator lights 76, a buzzer, and/or acoustical transmitter 77 that can also be used to communicate status and events to the user. In addition, controller 66 could also include hardware to implement one or more of the communication mechanisms described above with respect to embodiments that include cellular telephone functionality.

In the above-described embodiments of the present invention, the controller uses the microphone in the handheld device to receive commands from the user. However, that microphone or another microphone that is disposed on the outer surface of electrode 24 and is connected to the controller can also be used to listen to the sounds of the heart in the Precordial recording mode. The acoustical signal can be compared to the electrical signals to verify that the electrical signals are valid.

The order in which the user grips the electrodes can also be utilized to signal that the user is ready for the instrument to begin recording the next trace. For example, the device is normally programmed such that the user grips electrodes 21 and 22 with the right hand. Electrode 24 is then placed at the appropriate point on the user's body. When the user is ready to begin the next trace, the user places his left index finger on electrode 23. When controller 24 detects the user's finger on electrode 23, controller 24 begins recording the next trace and signals the user by activating a busy signal such as a buzzer, vibrator, or audio signal. When controller 24 completes the measurement, the busy signal is turned off.

The above discussion has assumed that the user is right handed. However, the present invention can be utilized by left handed individuals by suitably programming controller 24 at the time the present invention is setup for a particular user. In this case, the device is gripped in the left hand such that the thumb and index finger of the left hand are on electrodes 21 and 22 and the device is activated by the user placing the user's right index finger on electrode 23.

The above-described embodiments of the present invention utilize a handheld device such as a cellular telephone or PDA as part of the present invention. In such embodiments, the native functions and computing power of the handheld device can be used to augment the controller. For example, the telephone can be utilized as a modem to communicate the results of the ECG measurements to a physician or medical facility. In addition, in locations that include wireless network access, the cellular telephone or PDA can be used to connect to that network. However, embodiments in which the handheld device is merely a body that provides support for the electrodes and includes the controller discussed above can also be constructed. In this case, the body could include limited functionality such as a wireless transmitter for connecting the device to another device that provides the communication functions. For example, the handheld device or the controller could include a Bluetooth or other wireless transmitter that allows the controller to communicate with a wireless access point or a conventional cellular telephone or PDA that provides the connection to the physician or medical facility.

Various modifications to the present invention will become apparent to those skilled in the art from the foregoing description and accompanying drawings. Accordingly, the present invention is to be limited solely by the scope of the following claims.

What is claimed is:

1. An apparatus comprising:
    a handheld device having first, second, third, and fourth electrodes on an outer surface of said handheld device; and
    a controller configured to measure signals between said electrodes and to generate an ECG recording selected from the group consisting of standard lead traces and precordial traces when said first and second electrodes contact a first hand of a patient such that said first and second electrodes contact different locations on said first hand, said third electrode being in contact with a location on said patient's other hand and said fourth electrode contacts a point on said patient's body chosen from the group consisting of said patient's lower abdomen, one of said patient's legs, and a precordial measurement point on said patient, said point depending on said ECG recording.

2. The apparatus of claim 1 wherein said handheld device comprises a cellular telephone or a PDA.

3. The apparatus of claim 1 further comprising a port configured to accept a plug and four ECG leads, said controller being configured to utilize said four ECG leads in combination with said fourth electrode to measure a conventional ECG recording when said plug is inserted in said port, said four ECG leads being different from said first, second, third, and fourth electrodes.

4. The apparatus of claim 3 wherein said controller utilizes said four ECG leads and said fourth electrode to measure an ECG recording of one of said precordial traces.

5. The apparatus of claim 1 wherein said controller is configured to compare a newly generated ECG recording with a stored exemplary normal ECG recording and to generate an indication that indicates whether said newly generated ECG recording is consistent with said stored ECG recording.

6. The apparatus of claim 5 wherein said exemplary normal ECG recording comprises a previously recorded ECG recording.

7. The apparatus of claim 5 wherein said exemplary normal ECG recording comprises an average of a plurality of previously recorded ECG recordings.

8. The apparatus of claim 5 wherein said apparatus further comprises a communication device configured to send and receive messages from an external facility and wherein said controller is configured to communicate said newly recorded ECG recording to said external facility if said indication indicates that said newly generated ECG recording is inconsistent with said stored ECG recording.

9. The apparatus of claim 1 further comprising a microphone and speaker, wherein said controller is configured to communicate instructions to said user via said speaker and receives communications from said user via said microphone while said controller generates said ECG recording.

10. The apparatus of claim 1 further comprising a mode switch operable by a user of said apparatus to communicate which of a plurality of measurements are to be made next.

11. The apparatus of claim 1 further comprising a vibrator configured to cause said apparatus to vibrate when said vibrator is activated and wherein said controller is configured to actuate said vibrator when said controller is generating an ECG recording.

12. The apparatus of claim 1 further comprising a circuit configured to determine if said first, second, third, and fourth electrodes are in contact with said user's body.

13. The apparatus of claim 12 wherein said circuit comprises a pressure sensor associated with one of said electrodes, said pressure sensor measuring a force associated with said user gripping said apparatus at that electrode.

14. The apparatus of claim 12 wherein said circuit comprises an impedance measuring circuit configured to measure an impedance between pairs of said first, second, third, and fourth electrodes.

15. The apparatus of claim 1 wherein said controller is configured to provide placement information that depends on said ECG recording regarding locations on said patient's body that are to be brought into contact with said fourth electrode while said controller generates said ECG recording.

* * * * *